US011046819B2

(12) United States Patent
Nam et al.

(10) Patent No.: US 11,046,819 B2
(45) Date of Patent: Jun. 29, 2021

(54) SUPER ABSORBENT POLYMER AND METHOD FOR PRODUCING SAME

(71) Applicant: LG Chem, Ltd., Seoul (KR)

(72) Inventors: Dae Woo Nam, Daejeon (KR); Jun Kyu Kim, Daejeon (KR); Hyung Ki Yoon, Daejeon (KR); Tae Hwan Jang, Daejeon (KR); Bo Hyun Seong, Daejeon (KR); Yeon Woo Hong, Daejeon (KR); Su Jin Kim, Daejeon (KR); Seong Beom Heo, Daejeon (KR); Seon Jung Jung, Daejeon (KR); Ji Yoon Jeong, Daejeon (KR)

(73) Assignee: LG Chem, Ltd.

( * ) Notice: Subject to any disclaimer, the term of this patent is extended or adjusted under 35 U.S.C. 154(b) by 210 days.

(21) Appl. No.: 16/087,392

(22) PCT Filed: Dec. 28, 2016

(86) PCT No.: PCT/KR2016/015414
§ 371 (c)(1),
(2) Date: Sep. 21, 2018

(87) PCT Pub. No.: WO2018/110758
PCT Pub. Date: Jun. 21, 2018

(65) Prior Publication Data
US 2020/0010624 A1 Jan. 9, 2020

(30) Foreign Application Priority Data
Dec. 13, 2016 (KR) .................. 10-2016-0169385

(51) Int. Cl.
| | | |
|---|---|---|
| *C08J 3/07* | (2006.01) | |
| *C08J 3/075* | (2006.01) | |
| *C08K 3/013* | (2018.01) | |
| *A61L 15/60* | (2006.01) | |
| *C08J 3/12* | (2006.01) | |
| *C08J 3/24* | (2006.01) | |
| *C08K 5/06* | (2006.01) | |
| *C08K 5/09* | (2006.01) | |
| *C08L 33/06* | (2006.01) | |
| *C08K 3/30* | (2006.01) | |

(52) U.S. Cl.
CPC .............. *C08J 3/075* (2013.01); *A61L 15/60* (2013.01); *C08J 3/12* (2013.01); *C08J 3/247* (2013.01); *C08K 3/013* (2018.01); *C08K 5/06* (2013.01); *C08K 5/09* (2013.01); *C08L 33/06* (2013.01); *C08J 2300/14* (2013.01); *C08J 2333/08* (2013.01); *C08K 2003/3081* (2013.01); *C08L 2203/02* (2013.01)

(58) Field of Classification Search
CPC ....... C08J 3/07; C08J 3/075; C08J 3/12; C08J 3/247; C08J 2300/14; C08J 2333/08; A61L 15/60; C08K 3/013; C08K 5/06; C08K 5/09; C08L 33/06

USPC .......................................................... 502/402
See application file for complete search history.

(56) References Cited

U.S. PATENT DOCUMENTS

| | | | |
|---|---|---|---|
| 5,145,906 | A | 9/1992 | Chambers et al. |
| 5,563,218 | A | 10/1996 | Rebre et al. |
| 2002/0013394 | A1 | 1/2002 | Dairoku et al. |
| 2005/0137546 | A1 | 6/2005 | Joy et al. |
| 2007/0049689 | A1 | 3/2007 | Meyer et al. |
| 2007/0066167 | A1 | 3/2007 | Wada et al. |
| 2007/0129495 | A1 | 6/2007 | Mertens et al. |
| 2008/0075937 | A1 | 3/2008 | Wada et al. |
| 2009/0202805 | A1 | 8/2009 | Furno et al. |
| 2010/0331802 | A1 | 12/2010 | Yokoyama et al. |
| 2012/0091392 | A1 | 4/2012 | Daniel et al. |
| 2014/0193641 | A1 | 7/2014 | Torii et al. |
| 2015/0217270 | A1 | 8/2015 | Ueda et al. |
| 2015/0299404 | A1 | 10/2015 | Daniel et al. |
| 2016/0030921 | A1 | 2/2016 | Ryu et al. |
| 2016/0235882 | A1 | 8/2016 | Noh et al. |
| 2016/0361703 | A1 | 12/2016 | Jang et al. |
| 2017/0009026 | A1 | 1/2017 | Nam et al. |
| 2017/0066862 | A1 | 3/2017 | Matsumoto et al. |
| 2018/0056274 | A1 | 3/2018 | Lee et al. |
| 2018/0147557 | A1 | 5/2018 | Hwang et al. |

FOREIGN PATENT DOCUMENTS

| | | |
|---|---|---|
| CN | 101942065 A | 1/2011 |
| CN | 105683281 A | 6/2016 |
| CN | 105934451 A | 9/2016 |
| CN | 106414527 A | 2/2017 |
| CN | 107614575 A | 1/2018 |
| EP | 0615736 A1 | 9/1994 |
| EP | 0644211 A1 | 3/1995 |
| EP | 0744435 A1 | 11/1996 |
| EP | 0940148 A1 | 9/1999 |
| EP | 1153656 A2 | 11/2001 |
| EP | 1637105 A1 | 3/2006 |

(Continued)

OTHER PUBLICATIONS

Extended European Search Report including Written Opinion for Application No. EP16924097.5 dated Mar. 6, 2019.

(Continued)

*Primary Examiner* — Edward M Johnson
(74) *Attorney, Agent, or Firm* — Lerner, David, Littenberg, Krumholz & Mentlik, LLP

(57) ABSTRACT

A super absorbent polymer according to the present invention has excellent dryness while maintaining excellent absorption performance, and thus is preferably used for hygienic materials such as diapers, and can exhibit excellent performance.

3 Claims, No Drawings

(56) References Cited

FOREIGN PATENT DOCUMENTS

| | | |
|---|---|---|
| EP | 1730218 B1 | 12/2010 |
| EP | 2891520 A1 | 7/2015 |
| EP | 3075760 A1 | 10/2016 |
| EP | 3279241 A1 | 2/2018 |
| EP | 3406653 A1 | 11/2018 |
| EP | 2797566 B1 | 6/2019 |
| JP | H09051912 A | 2/1997 |
| JP | 2001137704 A | 5/2001 |
| JP | 2006176570 A | 7/2006 |
| JP | 2008297512 A | 12/2008 |
| JP | 2009057496 A | 3/2009 |
| JP | 2014505151 A | 2/2014 |
| KR | 100374127 B1 | 4/2003 |
| KR | 20070012623 A | 1/2007 |
| KR | 100876827 B1 | 1/2009 |
| KR | 101520127 B1 | 5/2010 |
| KR | 20140038998 A | 3/2014 |
| KR | 101495845 B1 | 2/2015 |
| KR | 20150048785 A | 5/2015 |
| KR | 20150087368 A | 7/2015 |
| KR | 20150117902 A | 10/2015 |
| KR | 20160061743 A | 6/2016 |
| KR | 20160076422 A | 6/2016 |
| KR | 20160115561 A | 10/2016 |
| KR | 20160128350 A | 11/2016 |
| KR | 20160141666 A | 12/2016 |
| WO | 9511932 A1 | 5/1995 |
| WO | 2005092956 A1 | 10/2005 |
| WO | 2006025586 A1 | 3/2006 |
| WO | 2013099174 A1 | 7/2013 |
| WO | 2013144026 A1 | 10/2013 |

OTHER PUBLICATIONS

Third Party Observation for Application No. PCT/KR2016/015414 dated Apr. 9, 2019.
Odian, George, Principles of Polymerization, 2nd Edition, John Wiley & Sons, Copyright 1981, p. 203, ISBN: 0-471-05146-2.
Schwalm, Reihold, UV Coatings—Basics, Recent Developments and New Applications, Elsevier Science, Dec. 21, 2006, p. 115, ISBN-10: 0444529799; ISBN-13: 978-0444529794.
International Search Report for PCT/KR2016/015414 dated Sep. 12, 2017.
Third Party Observation for Application No. EP20160924097 dated Jan. 7, 2020.
Bucholz et al., "Modern Superabsorbent Polymer Technology", Wiley-VCH, pp. 199-201, copyright 1998.
Ohinese Search Report for Application No. 201680083903.8, dated Jul. 31, 2020, pp. 1-3.
Buchholz et al., Modern Superabsorbent Polymer Technology, 1998, cover page, impressum, p. 19, p. 55, pp. 97-103, p. 167 and pp. 197-198, Wiley-VCH.
Matsumoto, Experimental Report concerning the reproduction of "Example 6" in EP 0744435 Al, dated Mar. 12, 2021, 4 pages.
Matsumoto, Experimental Report concerning the reproduction of "Example 8" in EP 2891520 A1, dated Mar. 11, 2021, 4 pages.
Notice of Opposition for Application No. EP16924097.5, dated Mar. 24, 2021, 43 pgs.
Worldwide Strategic Partners, Inda, Edana, Standard Test Methods for the Nonwovens Industry, Standard Test: WSP 241.2 (05) Standard Test Method for Superabsorbent Materials—Polyacrylate Superabsorbent Powders—Gravimetric Determination of Fluid Retention Capacity in Saline Solution After Centrifugation, 2005, 13 pages.

SUPER ABSORBENT POLYMER AND METHOD FOR PRODUCING SAME

CROSS-REFERENCE TO RELATED APPLICATION(S)

The present application is a national phase entry under 35 U.S.C. § 371 of International Application No. PCT/KR2016/015414, filed on Dec. 28, 2016, which claims the benefit of Korean Patent Application No. 10-2016-0169385, filed on Dec. 13, 2016, the disclosures of which are incorporated herein by reference.

TECHNICAL FIELD

The present invention relates to a super absorbent polymer having excellent dryness while maintaining excellent absorption performance, and a method for producing the same.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the content of pulp is reduced or pulp is not used at all is being actively advanced.

As described above, in the case of hygienic materials in which the pulp content is reduced or the pulp is not used, a super absorbent polymer is contained at a relatively high ratio and these super absorbent polymer particles are inevitably contained in multiple layers in the hygienic materials. In order for the whole super absorbent polymer particles contained in the multiple layers to absorb liquid such as urine more efficiently, it is necessary for the super absorbent polymer to basically exhibit high absorption performance and absorption rate.

For this purpose, the conventional super absorbent polymer uses a method of lowering the degree of internal crosslinking and increasing the degree of surface crosslinking. According to this method, however, the absorption rate may be increased, but after the super absorbent polymer is swollen by the absorbed liquid, the liquid is present on the surface of the super absorbent polymer, which causes a decrease in wearing feeling, a skin rash or the like.

As described above, the extent to which no liquid is present on the surface after the super absorbent polymer absorbs the liquid is referred to as "dryness". Therefore, there is a need to develop a super absorbent polymer having excellent dryness, without impairing the absorption performance and absorption rate of the super absorbent polymer.

DETAILED DESCRIPTION OF THE INVENTION

Technical Problem

It is one object of the present invention to provide a super absorbent polymer having excellent dryness while maintaining excellent absorption performance, and a method for producing the same.

Technical Solution

In order to achieve the above objects, the present invention provides a super absorbent polymer as follows:
the super absorbent polymer comprising:
a base polymer powder comprising a first cross-linked polymer of a water-soluble ethylenically unsaturated monomer having at least partially neutralized acidic groups; and
a surface cross-linked layer formed on the base polymer powder and comprising a second cross-linked polymer in which the first cross-linked polymer is further cross-linked via a surface crosslinking agent,
wherein an extractable content measured according to EDANA method No. WSP 270.2 is 13% by weight or less,
wherein an absorption rate (vortex) measured according to the measurement method of Vortex is 50 seconds or less, and
wherein a 6-hour dryness is 1.5 g or less.

The present invention also provides a super absorbent polymer as follows:
the super absorbent polymer comprising:
a base polymer powder comprising a first cross-linked polymer of a water-soluble ethylenically unsaturated monomer having at least partially neutralized acidic groups; and
a surface cross-linked layer formed on the base polymer powder and comprising a second cross-linked polymer in which the first cross-linked polymer is further cross-linked via a surface crosslinking agent containing ethyleneglycol diglycidyl ether, and an inorganic filler,
wherein a centrifuge retention capacity (CRC) is 28 g/g or more, and
wherein a 6-hour dryness is 1.5 g or less.

As described above, the super absorbent polymer according to the present invention has features that it has low extractable content and excellent dryness while having excellent absorption rate. The above described super absorbent polymer can be obtained by adjusting the preparation conditions of the super absorbent polymer as described below.

Hereinafter, embodiments of the present invention will be described in more detail.

Super Absorbent Resin

The water-soluble ethylenically unsaturated monomer constituting the first cross-linked polymer may be any monomer commonly used in the production of a super absorbent polymer. As a non-limiting example, the water-soluble ethylenically unsaturated monomer may be a compound represented by the following Chemical Formula 1:

$$R_1\text{—COOM}^1 \qquad \text{[Chemical Formula 1]}$$

in Chemical Formula 1,
$R_1$ is an alkyl group having 2 to 5 carbon atoms containing an unsaturated bond, and $M^1$ is a hydrogen atom, a monovalent or divalent metal, an ammonium group or an organic amine salt.

Preferably, the above-described monomer may be at least one selected from the group consisting of acrylic acid, methacrylic acid, and a monovalent metal salt, a divalent metal salt, an ammonium salt, and an organic amine salt thereof. When acrylic acid or a salt thereof is used as the water-soluble ethylenically unsaturated monomer, it is advantageous in that a super absorbent polymer having improved absorption property can be obtained. In addition, as the monomer, maleic anhydride, fumaric acid, crotonic acid, itaconic acid, 2-acryloylethanesulfonic acid, 2-methacryloylethanesulfonic acid, 2-(meth)acryloylpropane sulfonic acid, or 2-(meth)acrylamido-2-methylpropane sulfonic acid, (meth)acrylamide, N-substituted (meth)acrylate, 2-hydroxyethyl(meth)acrylate, 2-hydroxypropyl(meth)acrylate, methoxypolyethylene glycol(meth)acrylate, polyethylene glycol (meth)acrylate, (N,N)-dimethylaminoethyl(meth)acrylate, (N,N)-dimethylaminopropyl(meth)acrylamide, and the like may be used.

Here, the water-soluble ethylenically unsaturated monomers may have an acidic group, wherein at least a part of the acidic group may be neutralized. Preferably, the monomers may be those partially neutralized with an alkali substance such as sodium hydroxide, potassium hydroxide, ammonium hydroxide, or the like.

In this case, a degree of neutralization of the monomer may be 40 to 95 mol %, or 40 to 80 mol %, or 45 to 75 mol %. The range of the degree of neutralization may vary depending on the final physical properties. However, an excessively high degree of neutralization causes the neutralized monomers to be precipitated, and thus polymerization may not readily occur, whereas an excessively low degree of neutralization not only greatly deteriorates the absorbency of the polymer, but also endows the polymer with hard-to-handle properties, such as those of an elastic rubber.

The second cross-linked polymer is obtained by additionally crosslinking the surface of the base resin powder via a surface crosslinking agent. The surface crosslinking agent and the surface crosslinking method will be described later.

Meanwhile, the super absorbent polymer according to the present invention has an extractable content of 13% by weight or less as measured according to EDANA method No. WSP 270.2. The extractable content occurs mainly when the polymer chain forming a network is short during polymerization of the super absorbent polymer. The lower the value thereof is, the more excellent it is. Preferably, the extractable content measured according to EDANA method No. WSP 270.2 is 12% by weight or less, 11% by weight or less, or 10% by weight or less. In addition, the smaller the value thereof is, the more excellent it is. Thus, the lower limit of the extractable content is theoretically 0% by weight, but as an example, it is 1% by weight or more, 2% by weight or more, 3% by weight or more, 4% by weight or more, or 5% by weight or more.

Also, the super absorbent polymer according to the present invention has an absorption rate (vortex) of 50 seconds or less as measured according to the measurement method of Vortex. The absorption rate refers the time during which the vortex of the liquid disappears due to fast absorption when the super absorbent polymer is added to a physiological saline solution and stirred. This can define a fast absorption rate of the super absorbent polymer. Preferably, the absorption rate measured according to the measurement method of Vortex is 45 seconds or less, 40 seconds or less, or 35 seconds or less. In addition, the smaller the value thereof is, the more excellent it is. Thus, the lower limit of the absorption rate is theoretically 0 second, but as an example, it is 10 seconds or more, 20 seconds or more, or 25 seconds or more. Further, the concrete measurement method of Vortex will be further specified in the following embodiments.

Further, the super absorbent polymer according to the present invention has a 6-hour dryness of 1.5 g or less. The 6-hour dryness refers to the amount of moisture present on the surface when 6 hours lapse after 2 g of the super absorbent polymer absorbs and swells a moisture and the like. The concrete measurement method thereof will be further specified in the following embodiments. Preferably, the 6-hour dryness is 1.4 g or less, 1.3 g or less, 1.2 g or less, 1.1 g or less, or 1.0 g or less. In addition, the smaller the value of the dryness is, the more excellent it is. Thus, the lower limit of the 6-hour dryness is theoretically 0 g, but as an example, it is 0.1 g or more, or 0.2 g or more.

Further, the super absorbent polymer according to the present invention has a centrifuge retention capacity (CRC) for a physiological saline solution (0.9 wt % sodium chloride aqueous solution) for 30 minutes of 28 g/g or more. More preferably, the centrifuge retention capacity is 28.5 g/g or more, or 29.0 g/g or more, and 35 g/g or less, 34 g/g or less, or 33 g/g or less. The measurement method of the centrifuge retention capacity will be more specified in the following embodiments.

Further, preferably, the super absorbent polymer according to the present invention has an absorbency under pressure (0.3 AUP) at 0.3 psi for a physiological saline solution (0.9 wt % sodium chloride aqueous solution) for 1 hour of 25 g/g or more. The measurement method of the absorbency under pressure will be more specified in the following embodiments. More preferably, the 0.3 AUP is 26 g/g or more, 27 g/g or more, or 28 g/g or more, and 36 g/g or less, 35 g/g or less, 34 g/g or less, or 33 g/g or less.

In addition, the super absorbent polymer according to the present invention has a liquid permeability of 10 seconds to 150 seconds. The method for measuring the liquid permeability will be more specified in the following embodiments. Preferably, the liquid permeability is 20 seconds to 100 seconds.

Method for Producing Super Absorbent Polymer

The present invention provides a method for producing a super absorbent polymer as follows:

the method for producing a super absorbent polymer comprising the steps of:

crosslinking a water-soluble ethylenically unsaturated monomer having at least partially neutralized acidic groups in the presence of an internal crosslinking agent to form a hydrogel polymer containing a first crosslinked polymer;

drying, pulverizing and classifying the hydrogel polymer to form a base polymer power; and heat-treating and surface-crosslinking the base polymer powder in the presence of a surface crosslinking solution comprising water and a surface crosslinking agent to form a super absorbent polymer particle, wherein the water and surface crosslinking agent are used in an amount of 3.5 parts by weight or less and 0.15 parts by weight or less, respectively, based on 100 parts by weight of the base polymer powder.

Hereinafter, the above preparation method will be described in detail for each step.

(Step 1)

Step 1 is a step of forming a hydrogel polymer which is a step of crosslinking a monomer composition including an internal crosslinking agent, and a water-soluble ethylenically unsaturated monomer having at least partially neutralized acidic groups.

In this case, the water-soluble ethylenically unsaturated monomer is as described above. Further, the concentration of the water-soluble ethylenically unsaturated monomer in the monomer composition may be appropriately adjusted in consideration of the polymerization time, the reaction conditions and the like, and it may be preferably 20 to 90% by weight, or 40 to 65% by weight. These concentration ranges may be advantageous for adjusting the pulverization efficiency during pulverization of the polymer described below, without needing to remove unreacted monomers after polymerization by using the phenomenon of gel effect occurring in the polymerization reaction of the highly concentrated aqueous solution. However, when the concentration of the monomer is excessively low, the yield of the super absorbent polymer can be lowered. Conversely, when the concentration of the monomer is excessively high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

Further, as the internal crosslinking agent, any compound can be used without limitation as long as it enables introduction of a crosslink bond upon polymerization of the water-soluble ethylenically unsaturated monomer. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, ethylene glycol diglycidyl ether, propylene glycol, glycerin, or ethylene carbonate, which may be used alone or in combination of two or more thereof, but are not limited thereto.

Such internal crosslinking agent may be added at a concentration of about 0.001 to 1% by weight, based on the monomer composition. That is, if the concentration of the internal crosslinking agent is too low, the absorption rate of the polymer is lowered and the gel strength may become weak, which is undesirable. Conversely, if the concentration of the internal crosslinking agent is too high, the absorption capacity of the polymer is lowered and thereby is not preferred for an absorbent.

Further, in step 1, a polymerization initiator generally used in the production of a super absorbent polymer can be included. As a non-limiting example, as the polymerization initiator, a thermal polymerization initiator, a photo-polymerization initiator or the like may be used depending on the polymerization method. In particular, the thermal polymerization initiator can be used. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

As the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like. In addition, examples of the azo-based initiator may include 2,2-azobis(2-amidinopropane)dihydrochloride, 2,2-azobis-(N,N-dimethylene) isobutyramidine dihydrochloride, 2-(2-(carbamoylazo) isobutylonitril, 2,2-azobis[2-(2-imidazolin-2-yl)propane] dihydrochloride, 4,4-azobis-(4-cyanovaleric acid), and the like. More various thermal polymerization initiators are well disclosed in "Principle of Polymerization" written by Odian, (Wiley, 1981), p 203, the content of which is incorporated herein by reference.

The photo-polymerization initiator used herein may include, for example, one or more compounds selected from the group consisting of benzoin ether, dialkyl acetophenone, hydroxyl alkylketone, phenyl glyoxylate, benzyl dimethyl ketal, acyl phosphine and α-aminoketone. Among them, as a specific example of the acylphosphine, a commonly used lucyrin TPO, that is, 2,4,6-trimethyl-benzoyl-trimethyl phosphine oxide may be used. More various photo-polymerization initiators are well disclosed in "UV Coatings: Basics, Recent Developments and New Application" written by Reinhold Schwalm, (Elsevier, 2007), p 115, the content of which is incorporated herein by reference.

The polymerization initiator may be added in a concentration of about 0.001 to 1% by weight based on the monomer composition. That is, when the concentration of the polymerization initiator is too low, the polymerization rate may become slow and a large amount of residual monomer may be extracted in the final product, which is not preferable. Conversely, when the concentration of the polymerization initiator is higher than the above range, the polymer chains constituting the network become short, and thus the extractable content is increased and physical properties of the polymer may deteriorate such as a reduction in absorbency under load, which is not preferable.

In addition, the monomer composition may further include additives such as a foaming agent, a surfactant, a thickener, a plasticizer, a preservation stabilizer, an antioxidant, etc., if necessary.

Further, the foaming agent acts to cause foaming during polymerization to produce pores in the hydrogel polymer, thereby increasing the surface area. As the foaming agent, a carbonate can be used. As an example, sodium bicarbonate, sodium carbonate, potassium bicarbonate, potassium carbonate, calcium bicarbonate, calcium carbonate, magnesium bicarbonate or magnesium carbonate can be used.

Further, the foaming agent is preferably used in an amount of 1500 ppmw or less based on the weight of the water-soluble ethylenically unsaturated monomer. When the amount of the foaming agent used is more than 1500 ppmw, the pores become too large, the gel strength of the super absorbent polymer lowers and the density becomes low, which may cause problems in distribution and storage. Further, the foaming agent is preferably used in an amount of 500 ppmw or more, or 1000 ppmw or more, based on the weight of the water-soluble ethylenically unsaturated monomer.

Further, the surfactant allows to induce uniform dispersion of the foaming agent to perform a uniform foaming when foaming, thereby preventing the gel strength from being lowered or the density from being lowered. As the surfactant, it is preferable to use an anionic surfactant.

Specifically, the surfactant includes $SO_3^-$ anion, and a compound represented by the following Chemical Formula 2 can be used.

R—$SO_3$Na   [Chemical Formula 2]

in Chemical Formula 2,

R is an alkyl having 8 to 16 carbon atoms.

Further, the surfactant is preferably used in an amount of 300 ppmw or less based on the weight of the water-soluble ethylenically unsaturated monomer. When the amount of the surfactant used exceeds 300 ppmw, the content of the surfactant in the super absorbent polymer increases, which is not preferable. Further, the surfactant is preferably used in an amount of 100 ppmw or more, or 150 ppmw or more, based on the weight of the water-soluble ethylenically unsaturated monomer.

Such a monomer composition can be prepared in the form of a solution in which raw materials such as the above-mentioned monomer, the polymerization initiator and the internal crosslinking agent are dissolved in a solvent.

In this case, any usable solvent can be used without limitation in the constitution as long as it can dissolve the above-mentioned raw materials. Examples of the solvent may include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

Further, the formation of the hydrogel polymer through polymerization of the monomer composition may be performed by a general polymerization method, and the process is not particularly limited. As a non-limiting example, the polymerization method are largely classified into a thermal polymerization and a photo-polymerization according to the type of the polymerization energy source, and the thermal polymerization may be carried out in a reactor like a kneader equipped with agitating spindles and the photo-polymerization may be carried out in a reactor equipped with a movable conveyor belt.

As an example, the monomer composition is injected into a reactor like a kneader equipped with the agitating spindles, and thermal polymerization can be performed by providing hot air thereto or heating the reactor, thereby obtaining the hydrogel polymer. In this case, the hydrogel polymer, which is discharged from the outlet of the reactor according to the type of agitating spindles equipped in the reactor, may be obtained as particles with a size of centimeters or millimeters. Specifically, the hydrogel polymer may be obtained in various forms according to the concentration of the monomer composition injected thereto, the injection speed, or the like, and the hydrogel polymer having a (weight average) particle diameter of 2 to 50 mm may be generally obtained.

As another example, when the photo-polymerization of the monomer composition is performed in a reactor equipped with a movable conveyor belt, a sheet-shaped hydrogel polymer may be obtained. In this case, the thickness of the sheet may vary depending on the concentration of the monomer composition injected thereto and the injection speed, and the polymer sheet is preferably controlled to have typically a thickness of 0.5 to 5 cm in order to secure the production speed or the like while enabling a uniform polymerization of the entire sheet.

In this case, the hydrogel polymer obtained by the above-mentioned method may have a water content of 40 to 80% by weight. Meanwhile, the "water content" as used herein means a weight occupied by moisture with respect to a total weight of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the drying conditions may be determined as follows: the drying temperature is increased from room temperature to about 180° C. and then the temperature may be maintained at 180° C., and the total drying time may be set to 20 minutes, including 5 minutes for the temperature rising step.

(Step 2)

Step 2 is a step of drying, pulverizing and classifying the hydrogel polymer prepared in step 1 to form a base polymer power, and the base polymer powder and the super absorbent polymer obtained therefrom are suitably prepared and provided so as to have a particle size of 150 to 850 μm. More specifically, at least 95% by weight of the base polymer powder and the super absorbent polymer obtained therefrom have a particle size of 150 to 850 μm, and fine powders having a particle size of less than 150 μm can be less than 3% by weight. As the particle size distribution of the base polymer powder and the super absorbent polymer is adjusted within the preferable range as described above, the super absorbent polymer finally produced can already exhibit the above-mentioned physical properties more satisfactorily.

Meanwhile, the method of proceeding the drying, grinding and classifying will be described in more detail below.

First, when drying the hydrogel polymer, a step of coarse pulverization may be further carried out before drying in order to increase the efficiency of the drying step, if necessary. A pulverizing machine used herein may include, but its configuration is not limited to, for example, any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

In this case, the coarse pulverizing step may be performed so that the hydrogel polymer has a particle size of about 2 mm to about 10 mm. Pulverizing the hydrogel polymer into a particle size of less than 2 mm is technically not easy due to a high water content of the hydrogel polymer, and a phenomenon of agglomeration may occur between the pulverized particles. Meanwhile, if the hydrogel polymer is pulverized into a particle size of larger than 10 mm, the effect of increasing the efficiency in the subsequent drying step may be insignificant.

The hydrogel polymer coarsely pulverized as above or immediately after polymerization without the coarsely pulverizing step is subjected to a drying step. At this time, the drying temperature may be 50 to 250° C. When the drying temperature is less than 50° C., it is likely that the drying time becomes too long or the physical properties of the super absorbent polymer finally formed is deteriorated. When the drying temperature is higher than 250° C., only the surface of the polymer is excessively dried, and thus fine powder may be generated during the subsequent pulverization process and the physical properties of the super absorbent polymer finally formed may be deteriorated. More preferably, the drying may be performed at a temperature of 150 to 200° C., and more preferably at a temperature of 160 to 190° C. Meanwhile, the drying step may be carried out for 20 minutes to 15 hours, in consideration of the process efficiency, but is not limited thereto.

In the drying step, any drying method may be selected and used without limitation in the constitution if it is a method commonly used in the relevant art. Specifically, the drying step may be carried out by a method such as hot air supply, infrared irradiation, microwave irradiation or ultraviolet irradiation. When the drying step as above is finished, the water content of the polymer may be 0.05 to 10% by weight.

Next, a step of pulverizing the dried polymer obtained through such a drying step is carried out.

The polymer powder obtained through the pulverizing step may have a particle diameter of 150 μm to 850 μm. Specific examples of a pulverizing device that can be used to pulverize into the above particle diameter may include a ball mill, a pin mill, a hammer mill, a screw mill, a roll mill, a disc mill, a jog mill or the like, but it is not limited to the above-described examples.

Further, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of 150 μm to 850 μm is classified and only the polymer powder having such a particle diameter is subjected to the surface crosslinking reaction described later and finally commercialized.

In addition, it is preferable that the prepared base polymer powder has a centrifuge retention capacity (CRC) of 32 to 37 g/g.

(Step 3)

Step 3 is a step of crosslinking the surface of the base resin polymer prepared in step 2, which is a step of heat-treating and surface-crosslinking the base polymer powder in the presence of a surface crosslinking solution containing water and a surface crosslinking agent to form a super absorbent polymer particle.

Here, the kind of the surface crosslinking agent contained in the surface crosslinking solution is not particularly limited. As a non-limiting example, the surface crosslinking agent may be at least one compound selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol trimethylol propane, pentaerythritol, sorbitol, calcium hydroxide, magnesium hydroxide, aluminum hydroxide, iron hydroxide, calcium chloride, magnesium chloride, aluminum chloride, and iron chloride. Preferably, ethylene glycol diglycidyl ether is used.

In this case, the surface crosslinking agent may be used preferably in an amount of 0.15 parts by weight or less based on 100 parts by weight of the base polymer. If the amount of the surface crosslinking agent used exceeds 0.15 parts by weight, excessive surface crosslinking may proceed, and various physical properties, especially dryness, of the super absorbent polymer may be deteriorated. Preferably, the surface crosslinking agent is preferably used in an amount of 0.14 parts by weight or less, 0.13 parts by weight or less, 0.12 parts by weight or less, 0.11 parts by weight or less, or 0.10 parts by weight or less, based on 100 parts by weight of the base polymer. Further, the surface crosslinking agent is preferably used in an amount of 0.01 parts by weight or more, 0.02 parts by weight or more, 0.03 parts by weight or more, 0.04 parts by weight or more, or 0.05 parts by weight or more, based on 100 parts by weight of the base polymer.

Further, the water is preferably used in an amount of 3.5 parts by weight or less based on 100 parts by weight of the base polymer powder. If the amount of water used exceeds 0.15 parts by weight, excessive surface crosslinking may proceed, and various physical properties, especially dryness, of the super absorbent polymer may be deteriorated. Preferably, the water is preferably used in an amount of 3.4 parts by weight or less, 3.3 parts by weight or less, 3.2 parts by weight or less, 3.1 parts by weight or less, or 3.0 parts by weight or less, based on 100 parts by weight of the base polymer. Further, the water is preferably used in an amount of 0.1 part by weight or more, 0.2 parts by weight or more, 0.3 parts by weight or more, 0.4 parts by weight or more, or 0.5 parts by weight or more, based on 100 parts by weight of the base polymer.

Further, the surface crosslinking solution may further include aluminum sulfate. The aluminum sulfate may be included in an amount of 0.02 to 0.3 parts by weight based on 100 parts by weight of the base polymer.

Further, the surface crosslinking solution may contain an inorganic filler. The inorganic filler may include silica, aluminum oxide, or silicate. The inorganic filler may be included in an amount of 0.01 to 0.5 parts by weight based on 100 parts by weight of the base polymer powder.

In addition, the surface crosslinking solution may further include a thickener. If the surface of the base polymer powder is further crosslinked in the presence of the thickener as described above, it is possible to minimize the deterioration of the physical properties even after the pulverization. Specifically, as the thickener, at least one selected from a polysaccharide and a hydroxy-containing polymer may be used. The polysaccharide may be a gum type thickener, a cellulose type thickener and the like. Specific examples of the gum type thickener include xanthan gum, arabic gum, karaya gum, tragacanth gum, ghatti gum, guar gum, locust bean gum, *psyllium* seed gum, and the like. Specific examples of the cellulose type thickener include hydroxypropylmethyl cellulose, carboxymethyl cellulose, methylcellulose, hydroxymethyl cellulose, hydroxyethyl cellulose, hydroxypropyl cellulose, hydroxyethylmethyl cellulose, hydroxymethylpropyl cellulose, hydroxyethylhydroxypropyl cellulose, ethylhydroxyethyl cellulose, and methylhydroxypropyl cellulose. Meanwhile, specific examples of the hydroxy-containing polymer include polyethylene glycol, polyvinyl alcohol and the like.

Meanwhile, in order to perform the surface crosslinking, a method of placing the surface crosslinking solution and the base polymer into a reaction tank and mixing them, a method of spraying a surface crosslinking solution onto the base polymer, a method in which the base polymer and the surface crosslinking solution are continuously supplied in a continuously operating mixer and mixed, or the like can be used.

In addition, the surface crosslinking may be carried out at a temperature of 100 to 250° C., and may be continuously performed after the drying and pulverizing step proceeding at a relatively high temperature. At this time, the surface crosslinking reaction may be carried out for 1 to 120 minutes, or 1 to 100 minutes, or 10 to 60 minutes. That is, in order to prevent a reduction in physical properties due to damages of the polymer particles by excessive reaction while inducing the minimal surface crosslinking reaction, the surface modification step may be performed under the above-described conditions.

Advantageous Effects

As described above, the super absorbent polymer according to the present invention has excellent dryness while maintaining excellent absorption performance, and thus is preferably used for hygienic materials such as diapers, and can exhibit excellent performance.

DETAILED DESCRIPTION OF THE EMBODIMENTS

Hereinafter, preferred examples are provided for better understanding of the invention. However, these Examples are given for illustrative purposes only and are not intended to limit the scope of the present invention thereto.

Example 1

100 g of acrylic acid, 0.37 g of polyethylene glycol diacrylate (PEGDA, Mw=523) as a crosslinking agent, 0.15 g of sodium persulfate (SPS) as a thermal initiator, 0.008 g of phenylene bis(2,4,6-trimethylbenzoyl) as a UV initiator, 40 g of caustic soda (NaOH) and 127 g of water were mixed to prepare a monomer aqueous solution composition having a monomer concentration of 45.8 wt %. The monomer aqueous solution composition was introduced to a feeder of a polymerization reactor equipped with a continuously movable conveyer belt. While maintaining the polymerization atmospheric temperature at 80° C., the composition in the reactor was irradiated with ultraviolet light (at irradiation dose of 10 mW/cm$^2$) using a UV irradiation device and UV polymerization was carried out for 2 minutes to produce a hydrogel polymer.

The hydrogel polymer was transferred to a meat chopper and cut into a size of 0.05 cm to 1 cm. The water content of the cut hydrogel polymer was 47 wt %. The hydrogel polymer was then dried in a hot air dryer at 170° C. for 30 minutes, and the dried hydrogel polymer was pulverized using a pin mill type pulverizing device. Then, the resultant polymer was classified into a polymer having a particle size (average particle diameter size) of 150 μm to 850 μm using a sieve to prepare a base polymer.

Subsequently, to 100 parts by weight of the base polymer thus prepared, a surface crosslinking solution (2.5 parts by weight of water, 0.1 part by weight of ethyleneglycol diglycidyl ether (EX-810), 0.1 part by weight of aluminum sulfate 18 hydrate (Al-S), and 0.1 part by weight of silica (Aerosil A200)) was uniformly mixed, and then subjected to a surface crosslinking reaction at 140° C. for 30 minutes. After completion of the surface treatment, the resultant product was sieved to obtain a super absorbent polymer having a particle diameter of 150 to 850 μm. In the super absorbent polymer thus obtained, the content of fine powder having a particle size of 150 μm or less was less than 2% by weight. Meanwhile, the CRC (#30-50) of the prepared base polymer was 35.5 g/g.

Examples 2 to 5 and Comparative Examples 1 to 4

A super absorbent polymer was obtained in the same manner as in Example 1, except that PEGDA, SPS, and the composition of the surface crosslinking solution were set as shown in Table 1 below.

TABLE 1

| | PEGDA (ppmw) | SPS (ppmw) | Composition of surface crosslinking solution (phr) | | | |
|---|---|---|---|---|---|---|
| | | | Water | EX810 | Al—S | Aerosil |
| Comparative Example 1 | 3700 | 4000 | 4.0 | 0.2 | 0.1 | 0.1 |
| Comparative Example 2 | 4200 | 4000 | 4.0 | 0.2 | 0.1 | 0.1 |
| Example 1 | 3700 | 1500 | 2.5 | 0.1 | 0.1 | 0.01 |
| Example 2 | 3700 | 1500 | 2.0 | 0.07 | 0.1 | 0.05 |
| Example 3 | 2900 | 1000 | 3.0 | 0.1 | 0 | 0.1 |
| Example 4 | 1700 | 1500 | 2.0 | 0.1 | 0.1 | 0.1 |

Experimental Example: Evaluation of Physical Properties of Super Absorbent Polymer The physical properties of the super absorbent polymer prepared in Examples and Comparative Examples were evaluated by the following methods.

(1) Centrifuge Retention Capacity (CRC)

The centrifuge retention capacity(CRC) by water absorption capacity under a non-loading condition was measured for the super absorbent polymers of Examples and Comparative Examples in accordance with EDANA (European Disposables and Nonwovens Association) method No. WSP 241.3.

Specifically, $W_0$ (g, about 0.2 g) of the super absorbent polymers of Examples and Comparative Examples were uniformly put in a nonwoven fabric-made bag, followed by sealing. Then, the bag was immersed in a physiological saline solution composed of 0.9 wt % aqueous sodium chloride solution at room temperature. After 30 minutes, water was removed from the bag by centrifugation at 250 G for 3 minutes, and the weight $W_2(g)$ of the bag was then measured. Further, the same procedure was carried out without using the super absorbent polymer, and then the resultant weight $W_1(g)$ was measured.

Using the respective weights thus obtained, CRC (g/g) was calculated according to the following Mathematical Formula 1.

$$CRC(g/g)=\{[W_2(g)-W_1(g)-W_0(g)]/W_0(g)\} \quad \text{[Mathematical Formula 1]}$$

in Mathematical Formula 1, $W_0(g)$ is an initial weight(g) of the super absorbent polymer, $W_1(g)$ is the weight of the device not including the super absorbent polymer, measured after immersing and absorbing the same into a physiological saline solution for 30 minutes and then dehydrating the same by using a centrifuge at 250 G for 3 minutes, and $W_2(g)$ is the weight of the device including the super absorbent polymer, measured after immersing and absorbing the super absorbent polymer into a physiological saline solution at room temperature for 30 minutes and then dehydrating the same by using a centrifuge at 250 G for 3 minutes.

In addition, with respect to the respective base polymers produced in the preparation process of Examples and Comparative Examples, CRC (BR CRC) was measured in the same manner as described above.

(2) Extractable Contents (16 hr E/C)

The extractable contents were measured by the same method as described in EDANA (European Disposables and Nonwovens Association) method No. WSP 270.2.

Specifically, 1.0 g of the super absorbent polymer was put in 200 g of a 0.9 wt % NaCl solution, and then swollen for 16 hours while stirring at 500 rpm. The aqueous solution was filtered out through a filter paper. The filtered solution was primarily titrated to pH 10.0 with 0.1 N caustic soda solution, and then back-titrated to pH 2.7 with a 0.1 N hydrogen chloride solution. From the amount required during neutralization, the uncrosslinked polymer substance was calculated and measured as the extractable content.

(3) Dryness 2 g of the super absorbent polymer was put in a 500 mL beaker and 200 mL of distilled water at 22 to 24° C. was added thereto. After the super absorbent polymer was swollen, it was taken out and left at room temperature for 6 hours. Subsequently, after stacking five filter papers with a diameter of 5 cm, the filter paper was placed on the super absorbent polymer, and pressurized at 0.2 psi for 1 minute. The weight (dryness, g) of the distilled water absorbed by the filter pater was measured.

(4) Vortex (Absorption Rate)

50 mL of a 0.9 wt % NaCl solution was put in a 100 mL beaker, and then 2 g of each super absorbent polymer prepared in Examples and Comparative Examples was added thereto while stirring at 600 rpm using a stirrer. Then, the vortex time was calculated by measuring the amount of time until a vortex of the liquid caused by the stirring disappeared and a smooth surface was formed, and the result was shown as the vortex removal time.

50 mL of a 0.9 wt % NaCl solution was put in a 100 mL beaker, to which a magnetic bar with a size of 30 mm (polygon type with a length of 30 mm and a thickness of 8 mm) was added. While stirring at 600 rpm using a magnetic stirrer, 2.0 g of the super absorbent polymers prepared in Examples and Comparative Examples were respectively added. Then, the vortex time was calculated by measuring the amount of time until a vortex of the liquid caused by the stirring disappeared and a smooth surface was formed, and the result was shown as the vortex removal time (absorption rate; vortex).

(5) Absorbency Under Pressure (AUP)

The absorbency under pressure (AUP) of the super absorbent polymers of Examples and Comparative Examples was measured in accordance with EDANA (European Disposables and Nonwovens Association) method No. WSP 242.3.

Specifically, a 400 mesh stainless screen was installed at the bottom of a plastic cylinder having an inner diameter of 60 mm. $W_0$(g, 0.90 g) of the super absorbent polymers obtained in Examples and Comparative Examples were uniformly scattered on the stainless screen under a condition of a temperature of 23±2° C. of and a relative humidity of 45%. Then, a piston capable of further providing a load of 0.3 psi uniformly was designed so that the outer diameter was slightly smaller than 60 mm and thus it could move freely up and down without any gap with the inner wall of the cylinder. At this time, the weight $W_3$(g) of the device was measured.

A glass filter having a diameter of 125 mm and a thickness of 5 mm was placed in a Petri dish having a diameter of 150 mm, and a physiological saline solution composed of 0.90 wt % sodium chloride was poured until the surface level became equal to the upper surface of the glass filter. Then, a sheet of filter paper having a diameter of 120 mm was placed on the glass filter. The measuring device was placed on the filter paper, so that the liquid was absorbed under load for one hour. After one hour, the measuring device was lifted and the weight $W_4$(g) was measured.

Using the respective weights thus obtained, AUP (g/g) was calculated according to the following [Mathematical Formula 2.

$$\text{AUP}(g/g)=[W_4(g)-W_3(g)]/W_0(g) \qquad \text{[Mathematical Formula 2]}$$

in Mathematical Formula 2, $W_0$(g) is an initial weight (g) of the super absorbent polymer, $W_3$(g) is the total sum of a weight of the super absorbent polymer and a weight of the device capable of providing a load to the super absorbent polymer, and $W_4$(g) is the total sum of a weight of the super absorbent polymer and a weight of the device capable of providing a load to the super absorbent polymer, after absorbing a physiological saline solution to the super absorbent polymer under a load (0.9 psi) for 1 hour.

(6) Liquid Permeability

In a state where a piston was introduced in a chromatography tube (F20 mm), the liquid surface was displayed as a 20 ml mark line and a 40 ml mark line. Then, water was inversely introduced in a chromatography tube so that bubbles are not generated between a glass filter and a cork at the bottom of the chromatography tube, filling the tube for approximately 10 ml, and the chromatography tube was washed 2 to 3 times with salt water and filled with 0.9% salt water up to 40 ml or greater. A piston was introduced in the chromatography tube, a valve at the bottom was opened, and then the time (B) taken for the liquid surface decreasing from a 40 ml mark line to a 20 ml mark line was recorded.

10 mL of salt water was left in the chromatography tube, to which 0.2±0.0005 g of classified (30 # to 50 #) sample was added. Salt water was added thereto so that the salt water volume became 50 ml, and then the result was left for 30 minutes. After that, a piston with a weight (0.3 psi=106.26 g) was introduced in the chromatography tube, and the result was left for 1 minute. After opening a valve at the bottom of the chromatography tube, the time (T1) taken for the liquid surface decreasing from a 40 ml mark line to a 20 ml mark line was recorded. Thereby, the liquid permeability (time of T1-B) was measured.

The results of the above measurement are shown in Table 2 below.

TABLE 2

| | BR CRC (g/g) | CRC (g/g) | 16 hr E/C (wt %) | Dryness (g) | 0.3 psi AUP (g/g) | Liquid permeability (sec) |
|---|---|---|---|---|---|---|
| Comparative Example 1 | 35.1 | 30.1 | 19.1 | 2.5 | 29.7 | 38 |
| Comparative Example 2 | 32.8 | 28.1 | 16.8 | 1.7 | 30.8 | 18 |
| Example 1 | 35.5 | 30.5 | 12.5 | 0.9 | 28.1 | 23 |
| Example 2 | 34.3 | 30.3 | 11.3 | 0.7 | 28.5 | 45 |
| Example 3 | 34.3 | 29.1 | 9.5 | 0.6 | 30.3 | 31 |
| Example 4 | 34.5 | 30.5 | 7.8 | 0.3 | 29.1 | 21 |

From the results of Table 2, it was confirmed that the super absorbent polymers of Examples according to the present invention had low extractable content and excellent dryness while maintaining other physical properties equal to or higher than those of the super absorbent polymers of Comparative Examples.

The invention claimed is:

1. A method for producing a super absorbent polymer comprising the steps of:
crosslinking a water-soluble ethylenically unsaturated monomer having at least partially neutralized acidic groups in the presence of an internal crosslinking agent to form a hydrogel polymer containing a first crosslinked polymer;

drying, pulverizing and classifying the hydrogel polymer to form a base polymer power; and heat-treating and surface-crosslinking the base polymer powder in the presence of a surface crosslinking solution comprising water, a surface crosslinking agent, aluminum sulfate, and an inorganic filler to form a super absorbent polymer particle, wherein the water and surface crosslinking agent are used in an amount of 3.5 parts by weight or less and 0.15 parts by weight or less, respectively, based on 100 parts by weight of the base polymer powder, and wherein the surface crosslinking agent is at least one compound selected from the group consisting of ethylene glycol diglycidyl ether, polyethylene glycol diglycidyl ether, glycerol polyglycidyl ether, propylene glycol diglycidyl ether, and polypropylene glycol diglycidyl ether.

2. The method of claim 1, wherein
the base polymer powder has a centrifuge retention capacity (CRC) of 32 to 37 g/g.

3. The method of claim 1, wherein the super absorbent polymer particle has an extractable content measured according to EDANA method No. WSP 270.2 is 13% by weight or less, an absorption rate (vortex) measured according to the measurement method of Vortex is 50 seconds or less, and a 6-hour dryness is 1.5 g or less.

* * * * *